(12) United States Patent
Sakai et al.

(10) Patent No.: US 8,927,803 B2
(45) Date of Patent: Jan. 6, 2015

(54) ABSORBENT ARTICLE

(75) Inventors: Akane Sakai, Kanonji (JP); Yusuke Kawakami, Kanonji (JP); Ayako Akahira, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 515 days.

(21) Appl. No.: 13/257,333

(22) PCT Filed: Mar. 12, 2010

(86) PCT No.: PCT/JP2010/054714
§ 371 (c)(1),
(2), (4) Date: Nov. 2, 2011

(87) PCT Pub. No.: WO2010/107096
PCT Pub. Date: Sep. 23, 2010

(65) Prior Publication Data
US 2012/0078209 A1 Mar. 29, 2012

(30) Foreign Application Priority Data
Mar. 19, 2009 (JP) .................................. 2009-069020

(51) Int. Cl.
*A61F 13/15* (2006.01)
(52) U.S. Cl.
USPC .... 604/378; 604/379; 604/380; 604/385.101; 604/385.01
(58) Field of Classification Search
USPC .............. 604/378, 379, 380, 385.101, 385.01
See application file for complete search history.

(56) References Cited

FOREIGN PATENT DOCUMENTS

| JP | 03-178653 | 8/1991 |
|---|---|---|
| JP | 05-137750 | 6/1993 |
| JP | 06-254118 | 9/1994 |
| JP | 9-504210 | 4/1997 |
| JP | 2000-333987 | 12/2000 |
| JP | 2001-258935 A | 9/2001 |
| JP | 2003-159276 A | 6/2003 |
| JP | 2006-141721 A | 6/2006 |
| JP | 2008-154775 A | 7/2008 |
| WO | WO 95/11654 | 5/1995 |
| WO | WO 2007/069957 A1 | 6/2007 |

OTHER PUBLICATIONS

International Search Report from corresponding PCT application No. PCT/JP2010/054714 filed Jun. 1, 2010, 4 pgs.

*Primary Examiner* — Jacqueline F. Stephens
(74) *Attorney, Agent, or Firm* — Brinks Gilson & Lione

(57) ABSTRACT

To provide an absorbent article capable of sufficiently fulfilling a function of preventing lateral leakage even when a force is applied in the width direction (transverse direction) during wearing. An absorbent article comprising a liquid-pervious surface sheet, a liquid-impervious leakage-preventive sheet, and a liquid-retentive absorption body disposed between the surface sheet and the leakage-preventive sheet, wherein the absorption body comprises at least two layers, at least one of the layers is a first absorption body layer composed of a hydrophilic sheet and a super-absorbent polymer, and in the longitudinal middle area of the absorbent article, the width of the first absorption body layer is larger than the width of other absorption body layer(s). In the first absorption body layer, a plurality of hydrophilic sheets are stacked, the super-absorbent polymer is disposed between hydrophilic sheets, and the hydrophilic sheets are joined in a region where the super-absorbent polymer is not spread.

8 Claims, 5 Drawing Sheets

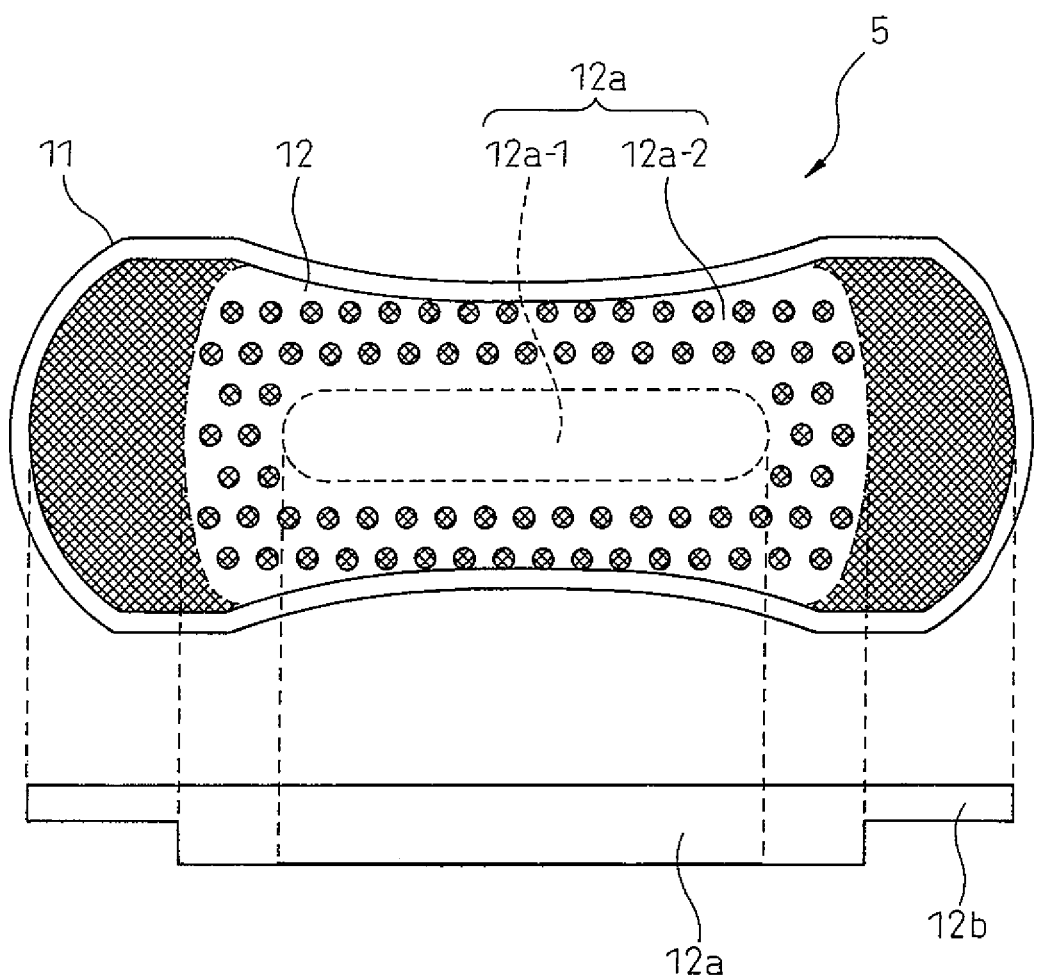

US 8,927,803 B2

ABSORBENT ARTICLE

RELATED APPLICATION

This application is a 35 U.S.C. §371 national phase filing of International Patent Application No. PCT/JP2010/054714, filed Mar. 12, 2010, through which and to which priority is claimed under 35 U.S.C. §119 to Japanese Patent Application No. 2009-069020, filed Mar. 19, 2009.

TECHNICAL FIELD

The present invention relates to an absorbent article. More specifically, the present invention relates to an absorbent article such as an incontinence pad or sanitary napkin, satisfying both the feeling of use between legs and absorption capacity.

BACKGROUND ART

In a general absorbent article, an absorption body being wide in the region corresponding to a part between legs similarly to the front and rear regions and completely rectangular in shape is used to impart sufficiently high absorption ability in a part between legs and thereby prevent lateral leakage.

The absorbent article disclosed in Patent Document 1 (Japanese Unexamined Patent Publication (Kokai) No. 2000-333987) is, in the longitudinal direction of the absorbent article, curved to recess from the contact surface side, has a constriction part where the side parts of the absorbent article at the position abutting on the excretory part are narrowed in the direction to the center in planar view, and has, in both longitudinal side parts, a solid part with the surface being curved to be convex toward the skin contact side. Therefore, in such a configuration, the curved shape fits the curved surface in the front-rear direction of the wear's body to prevent leakage from the front and rear ends of the absorbent article, and the constriction and the solid shape with a convex curved surface fit the curved surface of the groin to create no gap, thereby preventing leakage of the excrement from the circumferential edge part during wearing. In Patent Document 1, a rectangular absorption body having a narrower width than the width of the constriction part is used for the absorption layer.

Also, Patent Document 2 (Kokai No. 5-137750) discloses an hourglass-shaped napkin having a constriction part where the side parts of the absorbent article at the position abutting on the excretory part are narrowed in the direction to the center in planar view, wherein a narrowed constriction part is provided in a part of both longitudinal side parts also in the absorption layer. This napkin fits the wearer's narrow crotch and is effective in preventing deformation such as distortion and twisting.

RELATED ART

Patent Document

Patent Document 1: Kokai No. 2000-333987
Patent Document 2: Kokai No. 5-137750

SUMMARY OF THE INVENTION

Problems to be Solved by the Invention

In a conventional absorbent article having an absorption body which is wide in the region corresponding to a part between legs similarly to the front and rear regions and totally rectangular in shape, the absorption body is deformed due to a force applied in the width direction (transverse direction) during wearing and becomes bulky in a part between legs, which may impair the feeling of wearing and cause twisting and narrowing of the absorption surface, leading to leakage of the excrement due to failure in sufficiently capturing it.

The absorbent article of Patent Document 1 is, in the longitudinal direction, curved to recess from the skin contact surface, has a constriction narrowed in the width direction at a position abutting on the excretory part, and has, in both longitudinal side parts, a solid part with the surface being curved to be convex toward the skin contact side, and therefore, at a glance, the shape in the front-rear direction of a part between legs, which is convexly curved, seems to perfectly fit the concavely curved absorbent article, but during wearing, the shape of the absorbent article is deformed due to compression by clothing, underwear or the like or body pressure applied when the wearer sits, as a result, a uncomfortable feeling may develop or the absorption body may twist due to deformation and reduced in the absorption capacity.

Furthermore, in Patent Document 1, a narrow absorption body is used in conformity with the constriction in the width direction at the potion abutting on the excretory part and therefore, the excrement laterally spread at the excretion cannot be absorbed and may leak outside. As a countermeasure therefor, in Patent Document 1, a bank-like convex solid part is provided in the side parts to serve as a dam and lateral leakage is thereby prevented. However, there is a problem that the wearer may suffer discomfort of being wet by excrement, or, when a large amount of urine as in urge incontinence is excreted fast at one time, the excrement cannot be sufficiently prevented from climbing over the solid part with a convex curved surface and developing lateral leakage.

In Patent Document 2, thanks to an hourglass-shaped napkin, an effect of fitting the wear's narrow crotch part and preventing deformation such as distortion and twisting may be obtained, but the position abutting on the excretory part lacks the absorption body because the absorption body is constricted in the width direction and therefore, similarly to Patent Document 1, the excrement laterally spread at the excretion may be not absorbed and leak out of the absorption body.

Accordingly, an object of the present invention is to provide an absorbent article allowing the side part of the product to provide excellent feeling of use and being capable of sufficiently fulfilling a function of preventing lateral leakage even when a force is applied in the width direction (transverse direction) during wearing.

Means to Solve the Problems

In order to attain the above-described object, the present invention provides the followings.

(1) An absorbent article comprising a liquid-pervious surface sheet, a liquid-impervious leakage-preventive sheet, and a liquid-retentive absorption body disposed between the surface sheet and the leakage-preventive sheet, wherein the absorption body comprises at least two layers, at least one of the layers is a first absorption body layer composed of a hydrophilic sheet and a super-absorbent polymer, and in the longitudinal middle area of the absorbent article, the width of the first absorption body layer is larger than the width of the other absorption body layer(s).

(2) The absorbent article as described in (1) above, wherein in the first absorption body layer, a plurality of hydrophilic sheets are stacked, the super-absorbent polymer is disposed between hydrophilic sheets, and the hydrophilic sheets are joined in a region where the super-absorbent polymer is not spread.

(3) The absorbent article as described in (1) or (2) above, wherein the other absorption body layer(s) is(are) narrowly constricted in the longitudinal middle area of the absorbent article.

(4) The absorbent article as described in (1) to (3) above, the other absorption body layer layer(s) comprise(s) a second absorption body layer comprising an absorbent material and a super-absorbent polymer and the first absorption body is disposed closer to the skin side than the second absorption body layer.

(5) The absorbent article as described in (1) to (4) above, wherein a compressed groove is formed from the surface sheet toward the absorption body to integrate the surface sheet and the absorption body and in the first absorption body layer, the super-absorbent polymer is not distributed in the compressed groove part and is distributed inside and outside the compressed groove part.

(6) The absorbent article as described in (1) to (5) above, wherein the hydrophilic sheet of the first absorption body layer has a dry compression recovery ratio of 10% or more and a wet compression recovery ratio of 5% or more.

Effects of the Invention

According to the absorbent article of the present invention, an absorption body layer composed of a hydrophilic sheet and a super-absorbent polymer is used, the absorption body layer is used in combination with other absorption body layer(s) formed, for example, by mixing an absorbent fiber and a super-absorbent polymer, the former absorption body layer is wider than the other absorption body layer(s), and these layers are combined to configure an absorption body, whereby the product can satisfy both the feeling of use of the side part region and the absorption capacity and can provide an effect of preventing uncomfortable feeling or leakage.

BRIEF DESCRIPTION OF THE DRAWINGS

FIG. 6 shows a front view of the lower absorption body layer in the absorbent article of an Example of the present invention and a side view of the absorbent core in the lower absorption body layer.

MODE FOR CARRYING OUT THE INVENTION

Figure 1:
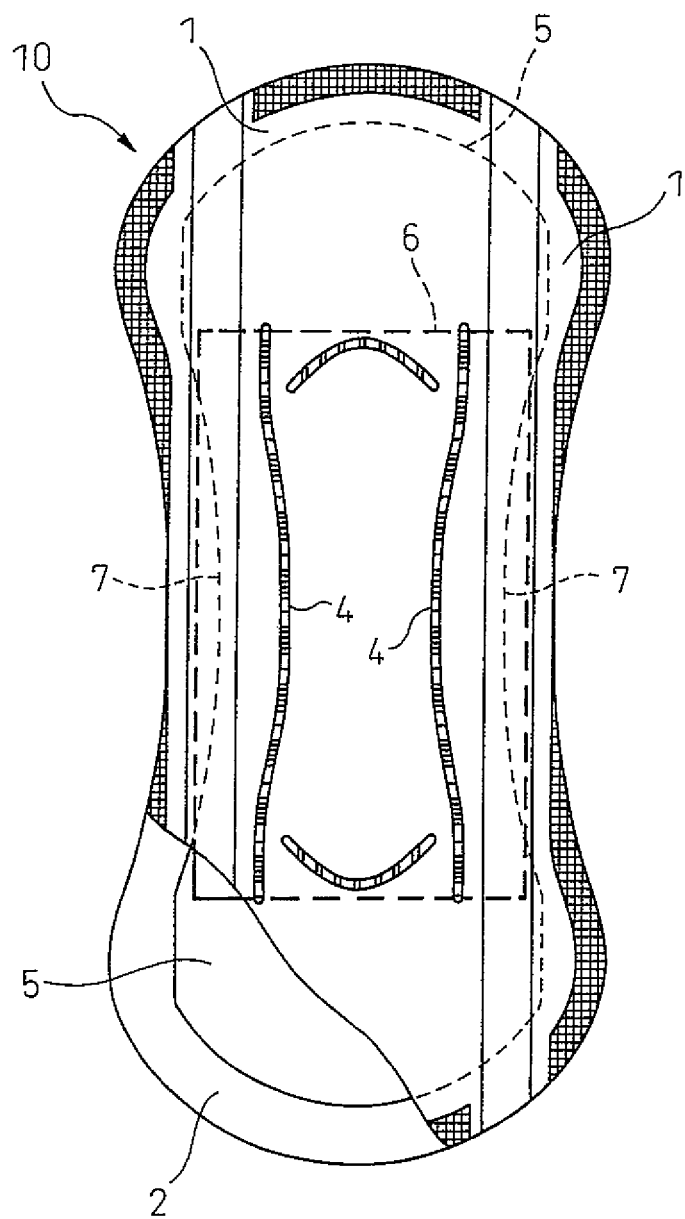
FIG. 1 shows a front view of the absorbent article of an Example of the present invention.

The embodiment of the absorbent article of the present invention is described in detail below by referring to the drawings.

Figure 2:
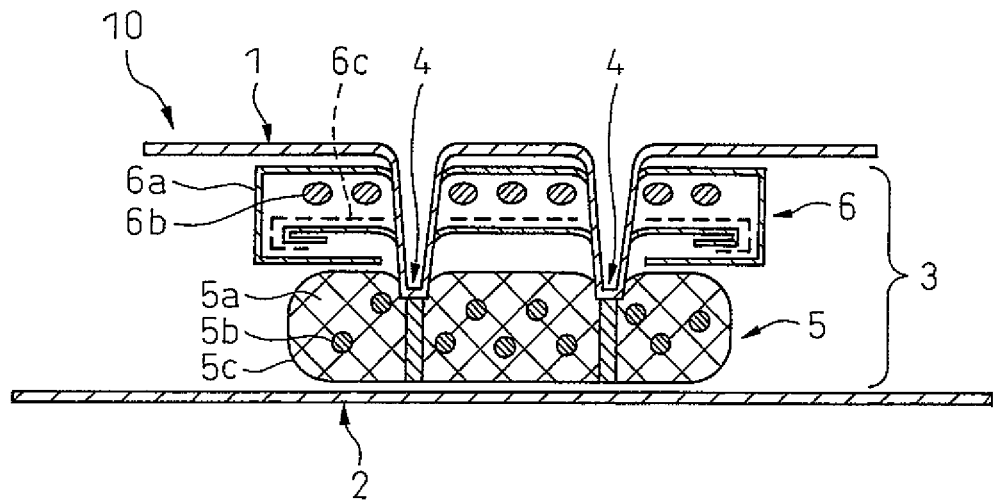
FIG. 2 shows a schematic lateral cross-sectional view of the absorbent article of an Example of the present invention.

FIG. 1 shows a front view of the absorbent article of an Example of the present invention, and FIG. 2 shows a lateral cross-sectional view of the absorbent article of FIG. 1. In FIG. 1, top/bottom is the longitudinal direction (belly-back direction), and right/left is the lateral direction (right leg-left leg direction).

As shown in FIGS. 1 and 2, in the absorbent article 10, a liquid-pervious surface sheet 1 is disposed on the wear's body side, a liquid-impervious leakage-preventive sheet 2 is disposed on the clothing side, and an absorption body 3 is disposed between the surface sheet 1 and the leakage-preventive sheet 2. In this working example, the absorption body 3 comprises two layers, i.e., an upper absorption body layer 6 as a first absorption body layer composed of a hydrophilic sheet 6a and a super-absorbent polymer 6b, and a lower absorption body layer (a main absorption body layer) 5 as another absorption body layer, but the absorption body layer may comprises two or more layers. The lower absorption body layer 5 is typically an absorption body layer where an absorbent fiber 5a and a super-absorbent polymer 5b are mixed. The upper absorption body layer 6 is formed to have, at least in the longitudinal middle area of the lower absorption body layer 5, a larger width than the width of the lower absorption body layer 5. The surface sheet 1 and the absorption body 3 are, in a state of being stacked one on another, integrated by a compressive groove (hinge) 4 from the surface sheet side.

The difference between the width of the upper absorption body layer 6 and the width of the lower absorption body layer 5, at least in the longitudinal middle area of the lower absorption body layer 5, is preferably at least 6 mm, more preferably 10 mm or more, more preferably from 10 to 40 mm or from 10 to 30 mm, and even more preferably from 10 to 20 mm, in total of both sides (on one side, half of this difference). If the difference in the width is less than 6 mm, sufficient absorption power against lateral leakage cannot be ensured, because narrowing of the lower-layer absorption body involves narrowing of the upper-layer absorption body. Alternatively, widening of the lower-layer absorption body involves widening of the upper-layer absorption body and although the absorption power may be ensured, an uncomfortable feeling is developed in a part between legs (groin). If this difference in the width exceeds 40 mm, the lower-layer absorption body is too narrow for the width between legs and sufficient absorption power cannot be ensured. In this case, if the width of the lower-layer absorption body is conformed with a part between legs, the upper-layer absorption body becomes excessively large and is protruded from underwear and leakage by flowing on the underwear side is causes an uncomfortable feeling.

As the lower absorption body layer 5, in general, an absorption body layer composed of an absorbent core formed by mixing an absorbent fiber 5a such as pulp and a super-absorbent polymer 5b, and a liquid-pervious tissue 5c covering the absorbent core, is preferably used.

In this working example, as shown in FIG. 1, assuming that the direction from belly toward back of a human body is a longitudinal direction and the direction from left leg toward right leg is a lateral direction, the lower absorption body layer 5 has a nearly rectangular shape longer in the belly-back direction (the width in the lateral direction is constant), and at least the absorbent core is in the shape of an hourglass having a narrowly constricted constriction part 7 in the longitudinal center area.

The constriction part 7 of the lower absorption body layer 5 has a smallest width in the absorption body layer and considering comfortable wearing in a part between legs, this part is preferably provided in a width of approximately from 30 to 80 mm. If the width exceeds 80 mm, the absorption body is disproportionated and becomes bulky during wearing and this may impair the feeling of wearing or let the absorption surface be twisted to inhibit absorption of the excrement. If the width is less than 30 mm, the feeling of wearing in a part between legs may be good but due to smaller width than the width between legs, the absorption power may be insufficient.

The upper absorption body layer 6 is described below.

The upper absorption body layer 6 is formed using a hydrophilic sheet 6a and a super-absorbent polymer 6b.

The hydrophilic sheet is a sheet having a hydrophilicity, which is composed of a nonwoven fabric, a porous plastic sheet or the like. In the case of a nonwoven fabric, a porous plastic sheet or the like, a hydrophilization treatment is applied, if desired. As the nonwoven fabric, a nonwoven fabric such as spun lace, spun bond, thermal bond, melt-blown, needle punch and air-through is used. Examples of the material fiber constituting the nonwoven fabric include a synthetic fiber such as olefin-based (e.g. polyethylene, polypropylene), polyester-based and polyamide-based, a regenerated fiber such as rayon and cupra, and a natural fiber such as cotton.

Examples of the super-absorbent polymer (SAP) include starch-based, acrylic acid-based or amino acid-based, particulate or fibrous polymers. The super-absorbent polymer is usually a pulverized material. Incidentally, SAP coated with an antimicrobial agent or the like may be also used.

Figure 3:
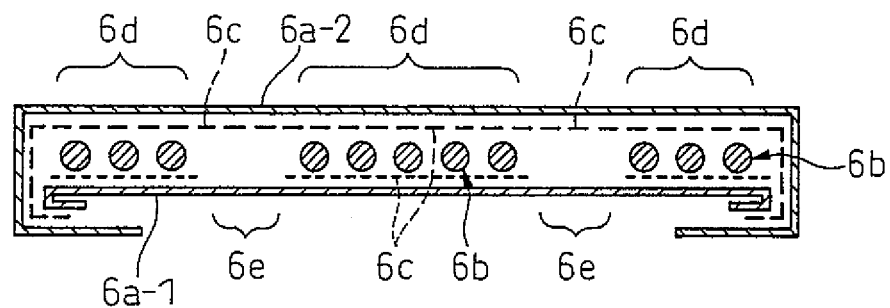
FIG. 3 shows a schematic lateral cross-sectional view of the upper absorption body layer in the absorbent article of an Example of the present invention.
Figure 4A:
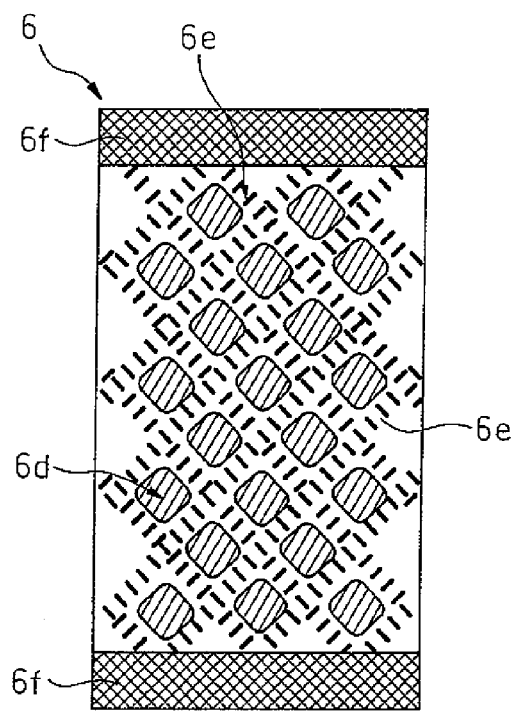
FIGS. 4A and 4B are a front view showing patterns of a joined region and a non-joined region in the upper absorption body layer in the absorbent article of Examples of the present invention.
Figure 4B:
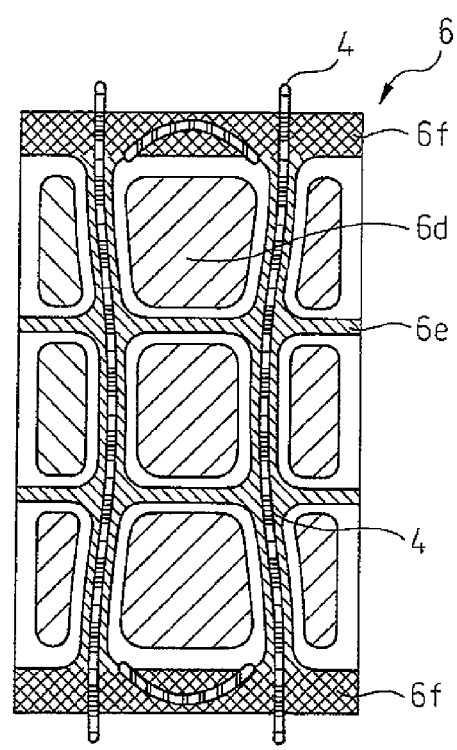

Referring to FIG. 3 and FIGS. 4A and 4B, in the upper absorption body layer 6, a super-absorbent polymer 6b is spread in a predetermined pattern on one side of a hydrophilic sheet 6a-1, another hydrophilic sheet 6a-2 is stacked to sandwich the super-absorbent polymer 6b therebetween, and the sheets are joined by a joining technique (for example, heat seal using a hot-melt adhesive 6c) in a portion 6e where the super-absorbent polymer 6b is not spread, whereby the layer is formed like a sheet.

The super-absorbent polymer 6b is preferably fixed to the hydrophilic sheet 6a by an adhesive 6c such as hot-melt adhesive, but the pulverized material may be present as it is in the pulverized state and covered by a hydrophilic sheet 6a without being fixed.

As the hydrophilic sheets sandwiching the super-absorbent polymer, one hydrophilic sheet may be folded and joined, or two hydrophilic sheets which are the same or different may be used as upper and lower sheets to sandwich the super-absorbent resin and joined.

In an embodiment, as shown in FIGS. 2 and 3, the upper absorption body layer may be formed by folding the end and edge parts of the hydrophilic sheet toward the center area. By folding these parts, even when a body pressure is excessively applied after absorption, the risk of letting the super-absorbent polymer jump out from the upper absorption body layer is eliminated, and the folding of end parts produces an effect of increasing the basis weight of the sheet material and enhancing the compression recovery property.

Referring to FIG. 1, at least in the longitudinal center area (middle area) of the absorbent article, the upper absorption body layer 6 has a size wider than the constriction part 7 of the lower absorption body layer 5. At this time, in the case where the lower absorption body layer 5 has a constriction part in the longitudinal middle area, the upper absorption body layer 6 may have a rectangular shape with a constant width in the lateral direction. Specifically, the upper absorption body layer 6 is preferably designed to have a width of 40 to 100 mm at least in the longitudinal center area (middle area) of the absorbent article. The length of the upper-layer absorption body can be appropriately set. In the case of the upper absorption body layer 6 being shorter than the length of the lower-layer absorption body, the liquid which cannot be captured by the upper-layer absorption body can be absorbed in the lower-layer absorption body, and in the case of being longer than the length of the lower-layer absorption body, front and rear end parts are formed by the upper-layer absorption body, making the absorbent article thinner, softer and easier to fit buttocks making broad movements.

The upper absorption body layer 6 contains a super-absorbent polymer 6b and therefore, can absorb and hold a liquid, and this layer functions as an absorption body layer. Also, the super-absorbent polymer 6b is held by hydrophilic sheets 6a, so that the super-absorbent polymer 6b can be formed as a sheet-like material. The hydrophilic sheet 6a is hydrophilic, and therefore can be wetted by excrement transmitted through the surface sheet 1, and this sheet does not inhibit but assists in the function of the super-absorbent polymer 6b of absorbing and holding the excrement.

Accordingly, when the sheet-like upper absorption body layer 6 formed using a hydrophilic sheet 6a has a size wider than the constriction part 7 of the lower absorption body layer 5 in the longitudinal center area of the absorbent article, the upper absorption body layer 6 comes to be present in a wide width between legs and can absorb also the excrement laterally spread at the excretion and prevent the excrement from leaking out of the absorption body.

In this way, the absorption body is configured by combining a lower absorption body layer 5 and an upper absorption body layer wider than the lower absorption body layer 5 in the longitudinal center area, so that the lower absorption body layer in a part between legs can be designed to have a narrow width in conformation with the width between legs and in turn, even when a force in the lateral direction is applied during wearing, the absorption body is less likely to be twisted and can maintain the absorption ability. Also, the absorption body is kept from being disproportionated in the direction to the center and becoming bulky, so that comfortable feeling of wearing can be maintained.

On the other hand, the center area of the lower absorption body layer is narrow, and this may be considered to reduce the absorption power in the side part region, but the upper absorption body layer is disposed in a wider manner than the lower absorption body layer and therefore, even when a large amount of urine is laterally spread, the urine can be stably absorbed by the upper absorption body layer.

Also, by taking a configuration where a super-absorbent polymer is sandwiched by hydrophilic sheets, the upper absorption body layer can be formed thinly while having a high absorption ability and even when formed in a wide width, does not give an uncomfortable feeling to the groin.

The upper absorption body layer 6 is formed using a hydrophilic sheet 6a and flexible and therefore, not only can be compressed in the sheet plane direction but also can have a property of, when the compression is released, repelling and recovering the original sheet form. As a result, the sheet-like upper absorption body layer 6 formed using a hydrophilic sheet 6a can follow the movement between legs, and the upper absorption body layer 6 can absorb also the excrement laterally spread at the excretion and more effectively prevent the excrement from leaking out of the absorption body.

Furthermore, the upper absorption body layer is disposed closer to the skin side than the lower absorption body layer, and this produces an effect that the excrement can be instantaneously absorbed by the high-absorbent polymer and a dry and comfortable feeling can be highly maintained. However, in the absorbent article of the present invention, the order of disposing the upper absorption body layer 6 and the lower absorption body layer 5 is not limited, and the order may be reversed between the upper layer and the lower layer.

The hydrophilic sheet 6a is preferably a sheet that is once defeated by an external force (in this case, a force applied to the inner side of the product from legs during wearing) and folded or disproportionated but when released from the external force, exhibits a high ability of returning to its original width. The hydrophilic sheet for use in the present invention can be evaluated by the following test method for the ability of returning to its original state upon release of an external force.

As the measurement apparatus, for example, a large compression tester, KES-G5, manufactured by Kato tech Co., Ltd. may be used. A test piece is sampled to have a size of 25 mm in width and 90 mm in length and become vertically longer in the MD (machine travel) direction of the stock sheet. The longitudinal end parts were overlapped by 10 mm and stapled together at 2 portions 5 mm inside both lateral edge parts to form a ring-shaped sample having a diameter of about 25 mm. The ring-shaped test sample is set on a compression measurement table with end parts being up and down, and the compression recovery ratio when compressed by 20 mm with a pressure-applying terminal of about 35 mm in diameter (area: 10 cm$^2$) is measured and taken as a dry compression recovery ratio R(d).

As for the compression recovery ratio, the height of the upper end part is measured when the test sample is fully recovered after the pressure-applying terminal is returned to its original position, and by taking a compression range of 20 mm as the base (100%), for example, when the recovery range is 5 mm (when the height of the test sample returns to 10 mm), the recovery ratio is calculated as 25%.

The hydrophilic sheet for use in the present invention preferably has a dry compression recovery ratio R(d) of 10% or more, more preferably 15% or more, still more preferably 20% or more.

In general, when folded or twisted during wearing and in this state, wetted by excrement, a sheet composed of an absorbent material tends to be less likely to return its original width due to hydrogen bonding. Accordingly, the hydrophilic sheet for use in the present invention is more preferably a sheet which can, even in a wetted state, easily return to its shape upon release of an external force. Therefore, the compression recovery ratio R(w) in a wet state is evaluated in the same manner as in the test method of a compression recovery ratio in a dry state except that the entire sample is immersed in water (tap water) (about 600 wt %), immediately pulled out and measured for compression.

The hydrophilic sheet for use in the present invention preferably has a wet compression recovery ratio R(w) of 5% or more, more preferably 10% or more, still more preferably 15% or more.

The dry compression recovery ratio R(d) and the wet compression recovery ratio R(w) of each of Sheets A, B, C and D are shown in Table 1.

TABLE 1

Compression Recovery Ratio of Hydrophilic Sheet

| Material Measured | (basis weight) | RD % | RW % |
|---|---|---|---|
| 1 Sheet A air-through | 25 g/m$^2$ | 27.1 | 16.6 |
| 2 Sheet B spunbond | 18 g/m$^2$ | 19.7 | 12.4 |
| 3 Sheet C air-laid | 75 g/m$^2$ | 9.3 | 1.4 |
| 4 Sheet D tissue | 16 g/m$^2$ | 21.8 | 0.0 |

RD: Dry compression recovery ratio
RW: Wet compression recovery ratio

In Table 1, Sheet A is an air-through nonwoven fabric of 25 g/m$^2$, and Sheet B is a point bond nonwoven fabric of 18 g/m$^2$, where the nonwoven fabric is composed of a non-adsorbent fiber and since the fiber itself does not absorb water, the compression recovery property in a wet T state can be maintained.

Sheet C is an air-laid composed of pulp and a binder, and Sheet D is a tissue. The air-laid sheet is hard and less likely to be compressed (not shown in the Table) but once folded by compression, can hardly return to its original width and since the sheet is composed of an absorbent fiber, the sheet in a wet state is softened by absorbing water and hardly recovered. The tissue similarly loses resilience after absorbing water and could not be measured for the wet compression recovery ratio.

From these results, the hydrophilic sheet is preferably a sheet which is, as in Sheets A and B, composed of a non-absorbent fiber, specifically, a core-sheath resin fiber of polyethylene (PE) and polypropylene (PP), and obtained by imparting hydrophilicity using a hydrophilizing agent to a through-air nonwoven fabric produced by melt-bonding fibers with hot air or a spunbond nonwoven fabric or point bond nonwoven fabric produced through bonding by heat embossing. The hydrophilic sheet can be selected from those having a basis weight of 10 to 50 g/m$^2$, a thickness of 0.3 to 5.0 mm, and a fineness of 1.8 to 4.0 dtex.

That is, the upper absorption body layer is configured to sandwich a super-absorbent polymer by hydrophilic sheets formed of a non-absorbent fiber, whereby even when wetted by excrement, the recovery force is less likely to decrease and the original width can be recovered in response to the movement of the wearer's body.

In the above, the compression recovery ratio is measured for a single sheet, but in the upper absorption body layer, at least two hydrophilic sheets as upper and lower sheets are used and even when the compression recovery ratio is the same as a single sheet, the compression recovery force as the entire upper absorption body layer becomes larger than in the case of a single sheet. Also, the worn absorbent article is not necessarily compressed as much as in the test conditions above and in this case, the recovery ratio is more increased.

FIGS. 4A and 4B show examples of the spread region 6d and the non-spread region 6e of the super-absorbent polymer 6b in the upper absorption body layer.

The upper absorption body layer 6 preferably has a spread region 6d and a non-spread region 6e of a super-absorbent polymer 6b, the hydrophilic sheets being joined by joining means in the non-spread region 6e. The hydrophilic sheets 6a-1 and 6a-2 are joined by joining means, whereby the super-absorbent polymer 6b can be confined to the non-spread region 6e.

In FIG. 4A, the non-spread region 6e of the upper absorption body layer 6 is formed in a tilted grid pattern, in the total area other than the front and rear end parts 6f. In FIG. 4A, an emboss is formed in the grid-like non-spread region 6e (6f), and the regions surrounded by the grid-like non-spread regions 6e (6f) are the super-absorbent polymer 6b-spread regions 6d. In FIG. 4B, the non-spread regions 6e of the upper, absorption body layer 6 include front and rear ends 6f and two non-spread regions 6e formed like a belt extending in each of the entire longitudinal and lateral directions, and the spared regions 6d of the super-absorbent polymer 6b are formed in a state of being divided into 9 parts. The non-spread regions 6e extending in the longitudinal direction is formed to conform with the pattern of compressed grooves (hinge) 4 by which the upper absorption body layer 6 is joined with the surface sheet 1, and in this configuration, the surface sheet 1 and the absorption body 3 are more unfailingly joined by the compressed groove 4.

The super-absorbent polymer 6b in the spread region 6d of the super-absorbent polymer 6b may be fixed to the hydrophilic sheet 6a by a hot-melt adhesive 6c or the like or may be allowed to freely move without being fixed. In the non-spread regions 6e of the super-absorbent polymer 6b, the hydrophilic sheets are joined together by a hot-melt adhesive, heat embossing or the like and therefore, a super-absorbent polymer is basically absent, but in practice, a small amount of a super-absorbent polymer may be present.

In this way, spread regions 6d and non-spread regions 6e of the super-absorbent polymer 6b are formed in the upper absorption body layer 6, whereby the super-absorbent polymer 6b is not distributed unevenly to one direction but is uniformly disposed throughout the hydrophilic sheet 6a (upper absorption body layer 6) and the excrement can be unfailingly absorbed even in the side parts of the longitudinal center area, where a lower absorption body layer 5 is not disposed.

That is, the upper absorption body layer 6 in the present invention is formed by disposing a super-absorbent polymer in a pattern and joining the hydrophilic sheets together in the super-absorbent polymer-non-spread regions, so that a super-absorbent polymer can be reliably disposed in the side part regions reduced in the absorption power and the excrement can be unfailingly absorbed in the regions.

The joining means can be selected from heat embossing, a hot-melt adhesive and the like, or these means may be used in combination. The heat emboss pattern is preferably a pattern ensuring that the embossed region is not hardened, the liquid perviousness is not impaired due to filming of the embossed part and even when the absorbent article is twisted or squeezed between legs during use, the joined part is not separated. Specifically, an emboss pattern where boxes of 0.5 to 5 mm square or dots of 0.5 to 5 mm in diameter are arranged in a houndstooth check pattern at intervals of 2 to 10 mm, is preferred (not shown).

In the case of using a hot-melt adhesive, for example, a general type of hot melt such as SIS, SBS and SEBS types may be used by employing a general hot-melt adhesive coating method such as coater, control seam, spiral and Summit systems.

Similarly, coating conditions making it possible to prevent scattering of the super-absorbent polymer 5b without impairing the flexibility are preferred. Specifically, hydrophilic sheets each having a basis weight of 3 to 10 g/m$^2$ are preferably joined together by coating the adhesive to a thickness of 0.5 to 5 mm by means of a coater in a comb pattern at a pitch of 1 to 5 mm.

Joining using a hot melt is preferably set to a mode where joining can be released by the swelling power of the super-absorbent polymer, because even in the case of absorbing a large amount of a body fluid, the absorption is less likely to be inhibited. Specifically, a hot-melt adhesive having a 180° peel adhesive force (JIS 2107) of 500 g to 4000 g is selected, and liquid-pervious sheets where, for example, the adhesive is coated in an amount of 1 to 10 g/m$^2$ to a thickness of 1 to 2 mm by a coater in a comb pattern at a pitch of 3 mm are laminated together, whereby the layer can be formed.

As shown in FIGS. 4A and 4B, the super-absorbent polymer 6b may be disposed in accordance with the idea of design of a commercial product to conform with the pattern of compressed grooves 4 which are provided to prevent twisting of the finished product, but in order to keep the emboss or compressed groove from engaging with the super-absorbent polymer as shown in FIG. 4B, patterning is preferably designed to locate the polymer from 2 to 5 mm inside the emboss or compressed groove pattern.

If the difference between the width of the non-spread region 6c of the super-absorbent polymer 6b and the width of the pattern of the compressed groove 4 is less than 2 mm, the super-absorbent polymer may be scattered at the time of spreading the super-absorbent polymer or due to vibration during production, allowing the super-absorbent polymer to engage with the emboss or compressed groove and failing in joining two sheets, or the hydrophilic sheet may be ruptured to expose the contents of the absorption body, such as super-absorbent polymer, on the surface, whereas if the difference exceeds 5 mm, the region absent of the super-absorbent polymer may be excessively broadened to impair the absorptivity.

Figure 5A:
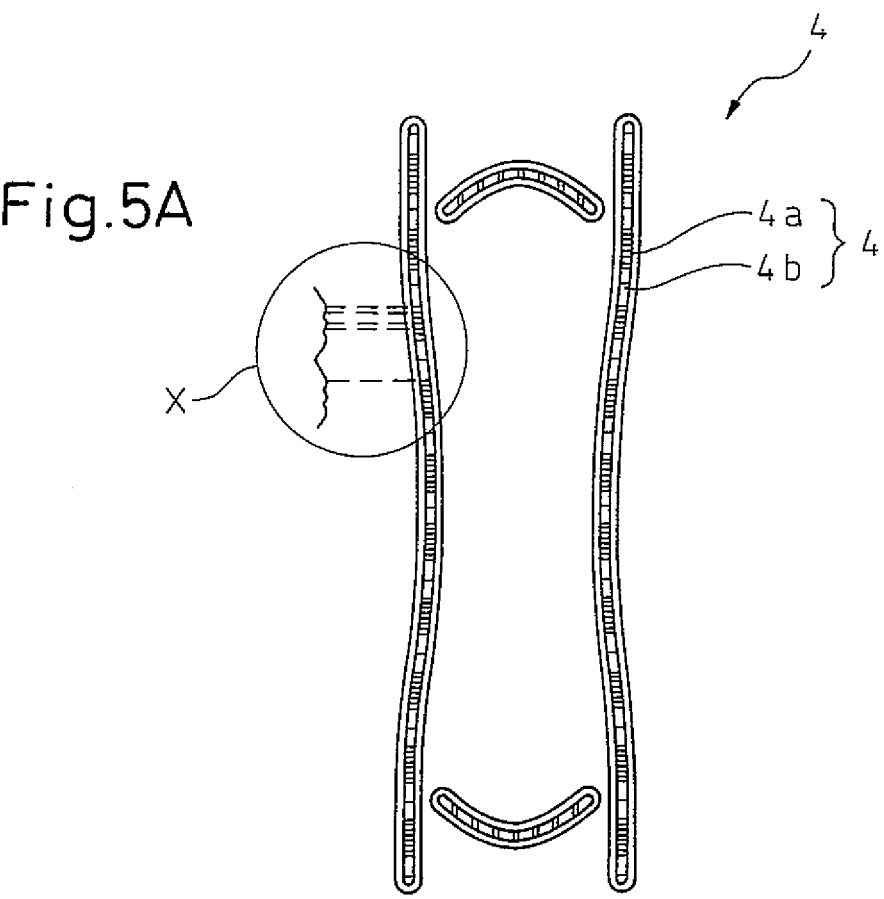
FIGS. 5A and 5B show a pattern of the compressed groove in the absorbent article of an Example of the present invention and a shape of the emboss for forming the groove.
Figure 5B:
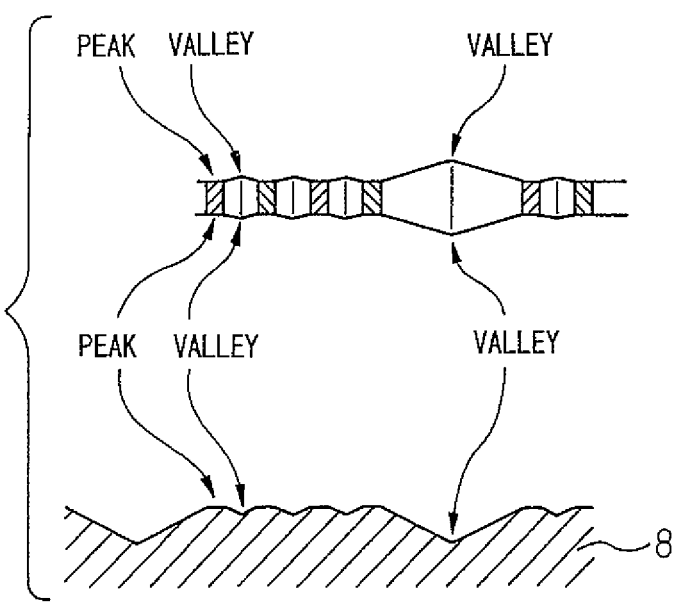

FIGS. 5A and 5B show an example of the pattern of a compressed groove (hinge) 4 for joining the surface sheet 1 with the absorption body 3 and the shape of an emboss for forming the pattern. FIG. 5A is a plan view, and FIG. 5B is an enlarged plan view of the part X of FIG. 5A and a cross-sectional view showing the shape of an emboss for hinge formation.

Referring to FIGS. 5A and 5B, the compressed groove is preferably formed, without continuing, such that a compressed part 4a and a non-compressed part 4b are repeated like dots, the compressed part 4a is formed by repeating small dot-shaped embosses (in FIG. 5A, four embosses), and the tip of each emboss 8 is composed of an obtuse peak and a valley, thereby preventing the surface sheet 1, the hydrophilic sheet 6a of the upper absorption body layer 6, or the like from rupture and letting the wearer feel good to the touch on the skin surface. FIG. 5B shows an enlarged view of a part X of the compressed groove 4 of FIG. 5A and a cross-sectional profile of the emboss for forming such a compressed groove.

As shown in FIG. 2, the compressed groove 4 extends from the surface sheet 1 to the upper absorption body layer 6 and the lower absorption body layer 5 and joins these. As described above, the non-spread region 6c of the super-absorbent polymer 6b of the upper absorption body layer 6 is caused to conform with the compressed groove 4 pattern, whereby the surface sheet 1 and the absorption body 3 are more reliably joined by the compressed groove 4.

Finally, other constituent materials are described below.

In the present invention, the lower absorption body layer 5 may be composed of a conventionally known absorber material that is utilized as a main absorption body in an absorbent article such as incontinence pad, sanitary napkin and disposable diaper. A representative absorbent material is a material containing a mixture of an absorbent fiber and a super-absorbent polymer.

The absorbent fiber includes a fluffed or nonwoven fabric-like pulp (including various fibers; hereinafter sometimes simply referred to as "pulp"). Examples of the fluffed pulp include a chemical pulp, a cellulose fiber, and an artificial cellulose fiber such as rayon fiber and acetate fiber. Examples of the air-laid nonwoven fabric include a nonwoven fabric where pulps and synthetic fibers are thermally fused or bonded with a binder. As the nonwoven fabric, a nonwoven fabric such as spun lace, spunbond, thermal bond, melt blown, needle punch and air-through may be used. Examples of the material fiber constituting the nonwoven fabric include a synthetic fiber such as olefin-based (e.g. polyethylene, polypropylene), polyester-based and polyamide-based, a regenerated fiber such as rayon and cupra, and a natural fiber such as cotton.

Examples of the super-absorbent polymer include starch-based, acrylic acid-based or amino acid-based, particulate or fibrous polymers. As the cushion, for example, a liquid-pervious paper or cellulose sheet part may be also used.

Specifically, a configuration where an absorbent fiber 5a such as pulp is mixed with a super-absorbent polymer 5b to form an absorbent core and the core is covered with a liquid-pervious material, particularly, a tissue 5c, is preferably used.

The liquid-pervious material covering the absorbent core may be a woven or nonwoven fabric formed of, for example, a cellulose such as cotton, a regenerated cellulose such as rayon and fibril rayon, a semisynthetic celluloses such as acetate and triacetate, a fibrous polymer, or a thermoplastic hydrophobic chemical fiber, other than a tissue.

The basis weight of the absorbent fiber 5a such as pulp is preferably from 100 to 800 g/m$^2$, and the mass ratio of the super-absorbent polymer 5b is preferably from 30 to 65% assuming that the absorbent fiber 5a is 100%.

The basis weight of the liquid-pervious material such as tissue covering a mixture where an absorbent fiber 5a and a super-absorbent polymer 5b are uniformly distributed in the entirety, is preferably from 12 to 30 g/m$^2$.

In addition, a hydrophilic sheet may be also used as other absorption body layers. Examples of the hydrophilic sheet include tissue, absorbent paper, and hydrophilized nonwoven fabric.

These absorbent materials are usually used in the form of a single-layer or a multilayer mat.

FIG. 6 shows a preferred example of the lower absorption body layer 5. This lower absorption body layer 5 has a configuration where an absorbent fiber such as pulp and a super-absorbent polymer are mixed to form an absorbent core and the core is covered with a liquid-pervious material, particularly, a tissue.

The upper view of FIG. 6 is a plan view of the lower absorption body layer 5, where 11 is the pattern of tissue, 12 is the pattern of absorbent core, and both have an hourglass shape with the longitudinal center being constricted.

The lower drawing of FIG. 6 is a side view of the absorbent core 12, where the absorbent core 12 is configured to be smaller in the thickness in the longitudinal front and rear end parts as compared with the main body part. It is preferred that the main body part 12a has a basis weight of 250 to 600 g/m$^2$ and as for the basis weight of the front and rear end parts 12b, the end part is formed by using a pulp having a basis weight of 200 to 500 g/m$^2$ and mixing a super-absorbent polymer in a ratio of 40 to 46%. The basis weight of the main body part 12a is set from the standpoint of ensuring sufficient absorptivity, and the basis weight of the front and rear end parts 12b is set in view of satisfying both absorptivity and comfort.

The emboss pattern is shown in the upper drawing of FIG. 6, where an emboss is not formed in the excretory part of the center area 12a-1 of the main body 12a of the lower absorption body layer 5 and an emboss is formed in a coarse dot pattern in other regions 12a-2 of the main body part 12a. Instead of a coarse dot pattern, a coarse grid-like pattern may be also used. The purpose of this emboss pattern is to reduce the thickness of the absorption body for decreasing elongation of the surface sheet 1 when forming a compressed groove 4, but if the density of the absorption body is excessively increased, the absorptivity (absorption speed) is impaired. For this reason, the emboss is formed in a coarse dot or grid-like pattern.

On the other hand, the emboss pattern in the front and rear end parts 12b of the lower absorption body layer 5 is preferably a fine grid-like pattern so as to attain a thin and soft finish for enhancing the comfort of the absorbent article. However, the area of the concave (non-compressed part) is preferably set to be larger than the area of the convex (compressed part) of the emboss.

By employing the above-described configuration, the lower absorption body layer can have a three-stage density gradient, that is, a region (center area of main body part) 12a-1 in the center area having a large basis weight and being absent of an emboss, a region (periphery of main body part) 12a-2 having coarse embosses despite a large basis weight, and a region (front and rear end parts) 12b having a small basis and being finely embossed.

The surface sheet 1 may be any sheet as long as it is liquid-pervious, does not damage the skin and can withstand friction with skin, and an air-through nonwoven fabric having a basis weight of approximately from 15 to 30 g/m$^2$ and being soft to the touch on skin, a spunbond nonwoven fabric, a hydrophilizing agent-imparted open-pore film, or a combination thereof may be used.

The back surface sheet 2 is preferably a polyethylene film which can keep the excrement from soaking into the underwear. Also, the shorts contact surface side of the back surface sheet 2 which is coated with a pressure-sensitive adhesive for fixing the sheet to shorts.

Although not described in the working examples above, if desired, a three-dimensional gather may be added on the surface sheet 1, a cushion layer (not shown) may be provided to intervene between the surface sheet 1 and the upper absorption body layer 6 or between the upper absorption body layer 6 and the lower absorption body layer 5, or a slip stopper coat and a separator may be provided on the back side of the back surface sheet 2.

In the foregoing pages, the present invention has been described on the basis of working examples where the absorbent article of the present invention is applied to an incontinence pad, but the present invention is also applicable to other absorbent articles such as sanitary napkin.

DESCRIPTION OF REFERENCE NUMERALS

1 Surface sheet
2 Leakage-preventive sheet
3 Absorption body
4 Compressed groove
5 Lower absorption body layer
5a Absorbent fiber
5b Super-absorbent polymer
5c Tissue
6 Upper absorption body layer
6a Hydrophilic sheet
6b Super-absorbent polymer
6c Hot-melt adhesive
6d Polymer-spread region
6e Polymer-non-spread region
7 Constriction part
10 Absorbent article

The invention claimed is:

1. An absorbent article comprising a liquid-pervious surface sheet, a liquid-impervious leakage-preventive sheet, and a liquid-retentive absorption body disposed between the surface sheet and the leakage-preventive sheet,
wherein said absorption body comprises at least two layers comprising a first absorption layer and a second absorption layer,
said first absorption layer comprises a stack of a plurality of hydrophilic sheets and a super-absorbent polymer disposed between the plurality of hydrophilic sheets, the second absorption layer comprises an absorbent core having a mixture of absorbent fibers and a super-absorbent polymer, and a liquid-pervious tissue covering the absorbent core, said second absorption layer being in a shape of an hourglass having a constriction part narrowly constricted in a longitudinal center area of the second absorption layer, said first absorption layer having a width that is larger than a width of said second absorption layer in a longitudinal middle area of the absorbent article, wherein a difference in width of said first absorption layer and said second absorption layer is from 6 mm to 40 mm, said first absorption layer being disposed closer to a skin side of the absorbent article than said second absorption layer, said first absorption layer and said second absorption layer being integrated together by embossing grooves extending from said surface sheet to said first absorption layer and second absorption layer, the super-absorbent polymer in said first absorption layer being spread in regions other than regions of the embossed grooves.

2. The absorbent article as claimed in claim 1, wherein in the first absorption body layer has a length that is shorter than a length of said second absorption layer.

3. The absorbent article as claimed in claim 2, wherein the hydrophilic sheet of the first absorption body layer is formed of a non-absorbent fiber.

4. The absorbent article as claimed in claim 1, wherein said first absorption layer has a length that is longer than a length of said second absorption layer.

5. The absorbent article as claimed in claim 1, wherein the width of said constriction part of said other absorption body layer(s) is from 30 to 80 mm, the width of the first absorption body layer in the portion overlapping therewith is from 40 to 100 mm, and the difference in the width therebetween is at least 6 mm in total of both sides.

6. The absorbent article as claimed in claim 1, wherein the hydrophilic sheet of the first absorption body layer has a dry compression recovery ratio of 10% or more and a wet compression recovery ratio of 5% or more.

7. The absorbent article as claimed in claim 1, wherein the hydrophilic sheet of the first absorption body layer has a dry compression recovery ratio of 15% or more and a wet compression recovery ratio of 10% or more.

8. The absorbent article as claimed in claim 1, which is a sanitary napkin.

* * * * *